United States Patent [19]

Korhonen et al.

[11] Patent Number: 5,669,910
[45] Date of Patent: Sep. 23, 1997

[54] CROSSLINK FOR IMPLANTABLE RODS

[75] Inventors: Francis J. Korhonen, Negaunee; Matthew N. Songer, Marquette, both of Mich.

[73] Assignee: Pioneer Laboratories, Inc., Marquette, Mich.

[21] Appl. No.: 582,166

[22] Filed: Jan. 2, 1996

[51] Int. Cl.⁶ .................................................. A61B 17/70
[52] U.S. Cl. ........................... 606/61; 606/72; 606/151
[58] Field of Search ............................ 606/61, 73, 104, 606/151

[56] References Cited

U.S. PATENT DOCUMENTS

| | | |
|---|---|---|
| 1,540,398 | 6/1925 | Jackson . |
| 1,939,813 | 12/1933 | Hagist . |
| 2,179,516 | 11/1939 | Patrick . |
| 3,162,719 | 12/1964 | Mulford . |
| 4,311,407 | 1/1982 | Doyle . |
| 4,653,481 | 3/1987 | Howland et al. . |
| 5,030,220 | 7/1991 | Howland . |
| 5,346,493 | 9/1994 | Stahurski et al. ............ 606/61 |
| 5,380,326 | 1/1995 | Lin .................................. 606/61 |
| 5,474,551 | 12/1995 | Finn et al. ..................... 606/61 |
| 5,487,742 | 1/1996 | Cotrel ............................ 606/61 |
| 5,496,321 | 3/1996 | Puno et al. ..................... 606/61 |
| 5,498,263 | 3/1996 | Dinello et al. ................. 606/61 |
| 5,534,200 | 7/1996 | Brumfield et al. ............. 606/61 |

FOREIGN PATENT DOCUMENTS

| | | | |
|---|---|---|---|
| 553424 | 8/1993 | European Pat. Off. ......... 606/61 |
| 2697743 | 5/1994 | France ............................ 606/61 |

OTHER PUBLICATIONS

Publications of AcroMed Corporation, ISOLA, Transverse Rod Connectors and the Modular Cross Connector (Date Unknown) Seven pages.
TSRH Crosslink System (Date Unknown) three pages.
Document entitled: Modulock Posterior Spinal Fixation believed to be originated from the Zimmer Corporation of Warsaw, Indiana.

*Primary Examiner*—Michael Buiz
*Assistant Examiner*—Julian W. Woo
*Attorney, Agent, or Firm*—Gerstman, Ellis & McMillin, Ltd.

[57] ABSTRACT

A crosslink member is provided for connecting a pair of surgical support rods in spaced, typically parallel relation. A first connector has a first recess, typically a bore, for receiving and retaining one of the pair of support rods, while a second connector has a second recess that may also be a bore, and which receives and retains the other of the support rods. The first connector is permanently attached to a crosslink rod that extends from the first connector to the second connector. The second connector has a third recess for receiving and retaining a portion of a crosslink rod. Retainers, such as set screws, are used to hold the two connectors of the crosslink member and the support rods together in a desired position. The third recess is closed by a cap with an interengaging sliding rail system.

11 Claims, 1 Drawing Sheet

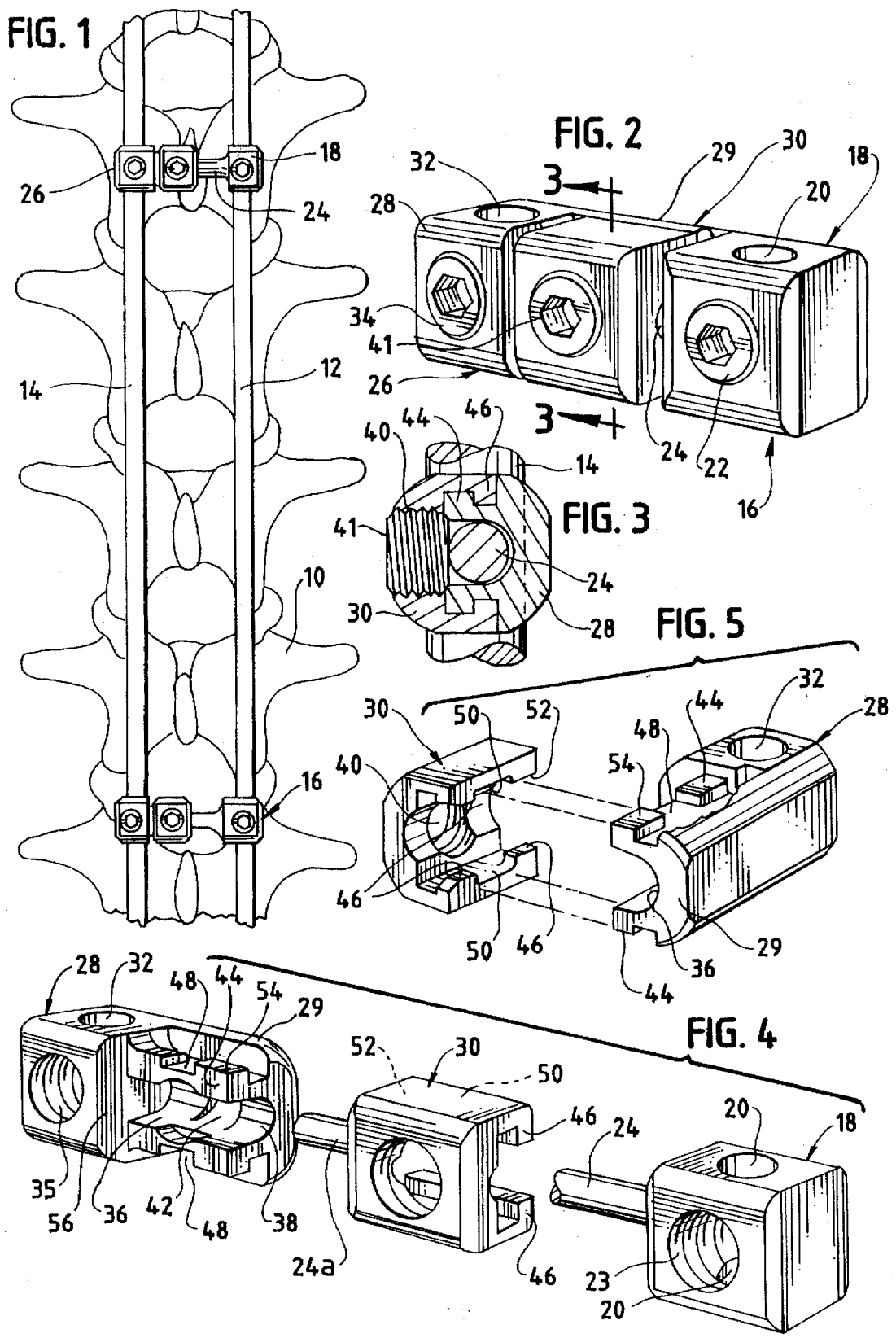

CROSSLINK FOR IMPLANTABLE RODS

BACKGROUND OF THE INVENTION

As shown for example in Howland U.S. Pat. No. 5,030,220, implantable rods are used for supporting broken spines or other bones in orthopedics. Further examples of such implantable rods and transverse connectors between the rods are the ISOLA (T.M.) transverse rod connectors of the AcroMed Corporation as well as the Modular Cross Connectors (T.M.) of the same company. These two commercial designs may be used to provide firm crosslinks between a pair of spinal rods, for example which are positioned on opposed sides of the spine for support of a severely broken back.

However, certain disadvantages of the prior art crosslinking systems exist in that they may be for one reason or another cumbersome for use and/or expensive. Also, the prior art crosslink systems for pairs of surgical support rods must come in different sizes, to accommodate pairs of surgical support rods of different spacings depending upon the size of the patient's spine and other factors.

DESCRIPTION OF THE INVENTION

By this invention, a single-sized crosslinking system for surgical support rods is provided, which may be used with a substantial variety of support rod spacings. This provides great convenience, in that it is not necessary to stock and to presterilize a series of crosslink members to be sure that one of proper size is sterilized and available during the operation, since it may not be readily predictable what the exact spacing for the respective support rods is going to be. By this invention, a single type of crosslink member may be processed for sizing, and then used in the surgery to secure a pair of surgical support rods at a desired spacing, despite the fact that the spacing may not be exactly predictable at the beginning of the surgery.

By this invention, a crosslink member is provided for connecting a pair of surgical support rods in spaced relation, typically parallel relation. The crosslink member comprises the following:

A first connector is provided, having a first recess for receiving and retaining one of the pair of support rods in secured manner. The first connector is permanently attached to a crosslink rod that extends from the first connector transversely away from the one support rod when the support rod occupies the first recess.

A second connector is also provided, having a second recess for receiving and retaining the other of the pair of support rods. The second connector also has a third recess for receiving and retaining a portion of the crosslink rod, which crosslink rod portion is spaced from the first connector. The same crosslink member may thus be used with surgical support rods of differing spacings, because the second connector can receive and grip differing portions of the crosslink rod in a manner appropriate to the desired spacing. The crosslink rod may be cut at the surgical site to eliminate an end portion in those cases where the rod is too long for the desired spacing.

Preferably, the third recess is open to the exterior on one end and one side thereof, in order to receive the crosslink rod typically after both the first and second connectors have been attached to their respective surgical support rods. Then, the surgical support rods may be spaced as desired, with a portion of the crosslink rod positioned in the third recess as described above. Retainers such as set screws or the like are provided for holding the crosslink member and support rods together in a desired position.

The second connector then preferably further comprises a cap, plus a connector body which defines the second and third recesses and is attached to one of the surgical support rods. The cap removably attaches to the connector body in a position that closes the one side of the third recess, to provide retention of the crosslink rod and the second connector.

Preferably, the connector body and cap of the second connector each define interconnectable rails, to permit longitudinal (transverse) sliding retention of the connector body and cap together into the desired position where the one side of the third recess is closed.

It is particularly desirable for the cap to be applied to the connector body with the respective rails in interengaging position, without the cap having to be placed completely at one end of the rails of the connector body, because, in that circumstance, the proximity of the first connector might interfere with that activity. To accomplish this, the rails of each of the connector body and cap define a central recess, the rails comprising opposed end rail sections typically on each side of the recess. The recess of each rail is long enough to permit the cap to be laterally placed (vertically placed or top loaded) into or out of the desired closing position at least in part by passing end rail sections of the respective rails through central recesses of the rails that they engage, typically followed by longitudinal movement of the cap along the connector body so that respective cap and body rail sections engage each other for retention, and the respective central recesses of the rails are spaced from each other.

Preferably, the cap defines a retainer such as an aperture and a threaded set screw conventionally rotatably mounted in the aperture to provide firm retention when desired between the cap and the crosslink rod.

Also, it is preferred for the first and second connectors (particularly the connector body) to each define retainers such as apertures and threaded set screws in the aperture, to provide firm connection between the connectors and respective support rods.

The set screws and their respective apertures may carry conventional set screw anti-back off features to prevent unplanned release of the connections provided against the support rods and crosslink rod by the set screws.

One may apply the crosslink member to a pair of surgical support rods which are in spaced relation by attaching a first connector having a first recess to one of the support rods, placing the support rod into the first recess and securing it there. The second connector, which has a second recess, may then be attached to the other support rod, placing the other support rod into the second recess and securing it there. The first connector is permanently attached to a crosslink rod, which is positioned to extend toward the second connector. A portion of the crosslink rod is placed into the third recess defined by the second connector and secured there, typically by a cap of the type described above. If necessary, the crosslink rod may be cut with a conventional surgical rod cutter, after it has been determined what the desired spacing between the two surgical support rods should be, to eliminate any excess length of the crosslink rod.

Thus, surgical support rods such as spinal rods may be secured together by one or more crosslink members and also secured to the spine or the like of a patient, to provide surgical support in an effective and efficient manner.

DESCRIPTION OF THE DRAWINGS

In the drawings, FIG. 1 is an elevational view of the spine of a patient, with a pair of surgical support rods positioned along the spine, the surgical support rods being locked together at a desired spacing by crosslink members in accordance with this invention;

FIG. 2 is an enlarged, perspective view of the crosslink member of this invention;

FIG. 3 is a sectional view taken along line 3—3 of FIG. 2;

FIG. 4 is an exploded, perspective view showing components of the crosslink member of the previous drawings; and FIG. 5 is an exploded, perspective view of the opposite side of the second connector shown in FIG. 4.

DESCRIPTION OF SPECIFIC EMBODIMENT

Referring to the drawings, FIG. 1 shows a schematic spine 10 of a patient in surgery, to which a pair of support rods 12, 14 are to be applied in spaced relation as shown. This spaced relation is maintained by the crosslink members 16 of this invention. The crosslink members 16 are attached to surgical support rods 12, 14 and maintain them in the desired spaced, parallel relation as shown.

Crosslink member 16, in this embodiment, comprises two major components, one of the components having two major pieces. One major component is first connector 18, which has a first recess 20, comprising a tubular bore in this embodiment, for receiving and retaining support rod 12. A set screw 22, which may be of conventional design, occupies a corresponding threaded retention aperture 23 that communicates with first bore or recess 20, so that first connector 18 may be firmly attached by set screw 22 to rod 12.

Also, first connector 18 is integrally attached to crosslink rod 24 by conventional welding or the like. The crosslink rod 24, 24a is shown in broken form in FIG. 4 for purposes of clarity, but is actually a continuous rod. It can be seen that crosslink rod 24 extends transversely away from first connector 18 and any support rod that occupies bore or recess 20.

Another major component of crosslink member 16 is second connector 26. Second connector 26, in this embodiment, comprises a connector body 28 and a cap 30, which may be attached to connector body 28. Also, in this embodiment, connector body 28 defines the second recess or bore 32, in which is received and retained the other support rod 14 as shown in FIG. 1. A set screw 34, occupying a threaded retention aperture 35 similar to aperture 23, is positioned to permit strong retention of rod 14 in bore 32 so that connector body 28 may be firmly retained on rod 14.

Connector body 28 also has an extension 29 which defines a third recess 36 for receiving and retaining portion 24a of crosslink rod 24 that is spaced from first connector 18 as previously stated. If in any given circumstance crosslink rod 24 is too long to fit into the third recess with a desired spacing of support rods 12, 14, crosslink rod 24 may be cut to shorten it, so that the end portion 24a of crosslink rod 24 is of a proper length.

As shown, third recess 36 is open not only at one end 38 but also at the side thereof. Cap 30 is provided to close the side of third recess 36, preferably after connector rod 24 has been placed therein. It can be seen that, if desired, connector rod 24 can be placed into third recess 36 from a lateral direction, which may not requires spacing first connector 18 and connector body 28 farther apart than their desired position as the support rod 24 is applied.

Then, cap 30 can be applied to close the side opening of third recess 36. Cap 30 also defines a threaded locking aperture 40 which is threaded in the manner of locking apertures 23, 35, and which receives a conventional set screw 41 which can lock crosslink rod 24 into tight, locked relation with second connector 26, with rods 12, 14 being spaced in a desired manner. Transverse groove 42 is provided in third recess 36 to permit a portion of rod 24 to flex slightly under the pressure of the set screw 41, so that crosslink rod 24 cannot be withdrawn from its position in third recess 36.

Connector body 28 defines a pair of longitudinally extending rails 44, positioned on either side of third recess 36. Cap 30 defines a corresponding, mating pair of rails 46, which are positioned to engage rails 44 in a manner to prevent lateral withdrawal of the cap while covering the side aperture of third recess 36. Also, when cap 30 is locked in position by set screw 41, crosslink rod 24 and its attached parts cannot be withdrawn, so that the support rods 12, 14 are retained together with a desired spacing.

Each of rails 44 and 46 permit sliding retention of cap 30 on connector body 28 to permit cap 30 to slide along the rails into the desired position shown in FIG. 2. Also, rails 44 each define a central recess 48, while rails 46 each define a central recess 50. Each of the recesses 48, 50 respectively separate opposed end sections of the rails 44, 46. Also, each recess 48, 50 is long enough to permit cap 30 to be laterally placed into or out of engagement with the rails, with end rail sections 52 of cap 30 passing through recesses 48, and end rail sections 54 of rails 44 passing through recesses 50, to bring the respective rails of connector body 28 and cap 30 into engagement. Then, cap 30 can be moved in sliding relation, parallel to the rails, into proximity with wall 56 of connector body 28, to put second connector 26 into its desired configuration of use as shown in FIG. 2.

Crosslink rod 24 is typically already placed in third recess 36 at this point, and set screw 41 is tightened to retain rod 24 in the desired position.

Thus, crosslink member 16 of this invention and rods 12, 14 are locked together in the desired relation, having a variable, locked, predetermined spacing for rods 12, 14.

The above has been offered for illustrative purposes only, and is not intended to limit the scope of this invention, which is as defined in the claims below.

That which is claimed:

1. A crosslink member for connecting a pair of surgical support rods in parallel spaced relation, which member comprises:

a first connector having a first recess for receiving and retaining one of said pair of support rods in secured manner, said first connector being permanently attached to a crosslink rod that extends from said first connector transversely away from said one support rod when the support rod occupies said first recess;

a second connector having a second recess for receiving and retaining the other of said pair of support rods, and a third recess for receiving and retaining a portion of said crosslink rod that is spaced from the first connector in a position where the other support rod and the crosslink rod have substantially coplanar longitudinal axes; and retainers for holding said crosslink member and support rods together in a desired position.

2. The crosslink member of claim 1 in which said third recess is open on one end and one side thereof, said second connector comprising a connector body and a cap that removably attaches to said connector body in a position that closes said third recess side.

3. The crosslink member of claim 2 in which said connector body and cap each define interconnectable rails to permit longitudinal sliding retention of the connector body and cap together into and out of said position, said rails each defining a central recess and opposed end rail sections, said recess of each rail being long enough to permit said cap to be laterally placed into or out of said position by passing respective end rail sections through respective central recesses.

4. The crosslink member of claim 1 in which said cap defines a first retainer comprising an aperture and a threaded set screw in said aperture to provide firm retention between said cap, said connector body, and said crosslink rod.

5. The crosslink member of claim 1 in which said first and second connectors each define second retainers comprising retention apertures and threaded set screws in said retention apertures to provide firm retention between said connectors and the respective support rods.

6. A crosslink member for supporting a pair of surgical support rods in parallel spaced relation, which member comprises:

a first connector having a first recess for receiving and retaining one of said pair of support rods in secured manner, said first connector being permanently attached to a crosslink rod that extends from said first connector transversely away from said one support rod when the support rod occupies said first recess;

a second connector having a second recess for receiving and retaining the other of said pair of support rods, said second connector having a third recess for receiving and retaining a portion of said crosslink rod that is spaced from the first connector in a position where the other support rod and the crosslink rod have substantially coplanar longitudinal axes, said third recess being open on one end and one side thereof, said second connector comprising a connector body which defines said second and third recesses, and a cap that removably attaches to said connector body in a position that closes said one side of the third recess, the said cap defining an aperture and a threaded set screw in said aperture to provide firm retention between said cap and said crosslink rod.

7. The crosslink member of claim 6 in which said first and second connectors each define retention apertures and threaded set screws in said retention apertures to provide firm retention between said connectors and the respective support rods.

8. The crosslink member of claim 7 in which said connector body and cap each define interconnectable rails to permit longitudinal sliding retention of said connector body and cap together into and out of said position.

9. The crosslink member of claim 8 in which said rails each define a central recess and opposed end rail sections, said recess of each rail being long enough to permit said cap to be top loaded into or out of said position at least in part by passing respective end rail sections through respective central recesses.

10. The method of connecting a pair of surgical support rods positioned in spaced relation, which method comprises connecting a first connector to one of said pair of support rods, and positioning a crosslink rod attached to said first connector to extend transversely away from said one support rod toward the other support rod;

attaching a second connector to the other of said pair of support rods;

placing said crosslink rod into engagement with said second connector in a position where the other support rod and the crosslink rod have substantially coplanar longitudinal axes, and sliding a removable cap in the direction parallel to said support rod into engagement with said second connector, and securing said removable cap, crosslink rod, and second connector together.

11. The method of claim 10 including the step of cutting said crosslink rod to a desired length to permit a desired spacing of said surgical support rods coupled with connection of said second connector with said crosslink rod.

* * * * *